Feb. 11, 1975 W. A. WARRINER Plant Pat. 3,682
ROSE PLANT
Filed July 23, 1973
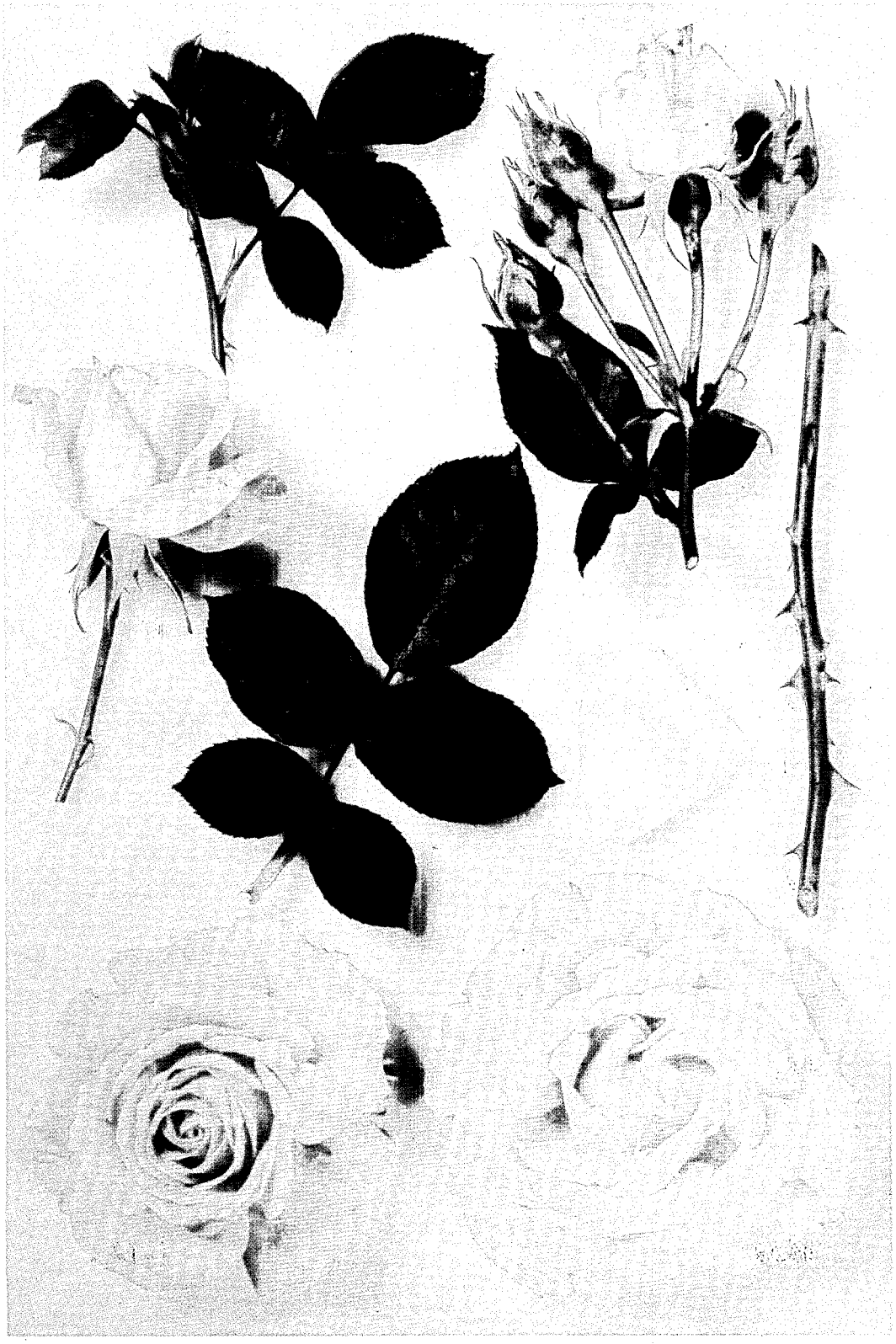

United States Patent

Plant Pat. 3,682

Patented Feb. 11, 1975

3,682

ROSE PLANT

William A. Warriner, Tustin, Calif., assignor to Jackson & Perkins Company, Medford, Oreg.

Filed July 23, 1973, Ser. No. 381,853

Int. Cl. A01h *5/00*

U.S. Cl.: Plt.—5 1 Claim

ABSTRACT OF THE DISCLOSURE

This present invention relates to a new and distinct cultivar of rose plant of the climber class which was originated by me by crossing the cultivar Fragrant Cloud, U.S. Plant Pat. 2,574 with pollen from the cultivar Tradition, unpatented.

The primary objective of this breeding was to produce a cultivar embodying the bushy, large foliage of Fragrant Cloud with the vigirous, nearly climbing characteristics of Tradition.

This objective was substantially achieved along with other desirable traits as evidenced by the following unique combinations of characteristics which are outstanding in the new cultivar and which distinguish it from its parents as well as from all other cultivars of which I am aware:

1. A vigorous "climbing" habit of growth.
2. Main growth canes terminate at about 5 or 6 feet, on young plants, into large clusters of blooms. Older plants, second and successive years, develop "climbing" canes of 10 or 12 feet in height before developing clusters of blooms.
3. When long canes are trained in a horizontal position, lateral growth develops the following spring from each node, making short stems terminating in one or a cluster of blooms.
4. The succession of blooms from the laterals of the older canes and terminals of new canes causes the cultivar to remain in bloom from spring until autumn.
5. A near immunity to Powdery Mildew and Rose Rust at Irvine, Calif.
6. A flower color of *Wilson's* Begonia when fully open fading slightly to Porcelain Rose when petals fall. This color is normally quite unblemished by excessive sun or adverse weather.
7. Large, abundant foliage.

Asexual reproduction of this new cultivar by budding, as performed at Wasco, Calif., shows that the foregoing characteristics and distinctions come true to form and are established and transmitted through succeeding propagations.

The accompanying drawing shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling.
- *Seed parent.*—Seedling of Fragant Cloud Plant Pat. 2,574.
- *Pollen parent.*—Tradition.

Classification:
- *Botanic.*—Rosa hybrid.
- *Commercial.*—Climber.

FLOWER

Observations were made at Irvine, Calif., in mid-June, 1973, in the afternoon.

Blooming habit: Rercurrent—continuous. Other habit—Blooms on terminals of large canes and on laterals.

Bud:
- *Size.*—¾" to 1" when petals start to unfurl.
- *Form.*—Short, globular.
- *Color.*—When sepals first divide—Lower side—Begonia (619); Upper side—Vermillion (18/1). When half blown; inside of petals—Vermillion (18/1); reverse of petals—Begonia (619). Base of petals—upper side—sharply defined segment of Primrose Yellow (601/2); lower side—large area Primrose Yellow (601/3) not sharply outlined.
- *Sepals.*—Color: Outer surface—mostly near Garnet Brown (00918/3). Inner surface—Scheeles Green (860/3) with white tomentum. Three appendaged sepals normally appendaged. Two unappendaged sepals hairy edged.
- *Receptacle.*—Color: Scheeles Green (860/3). Overlaid in irregular areas with Garnet Brown (00918/3). Shape: Funnel. Size: Large. Surface: Smooth.
- *Peduncle.*—Length: Short. Surface: Slightly prickly. Color: Same as Receptacle. Strength: Stiff, erect.
- *Opening.*—Petals fold outwardly with a slight curling back of petal tips.

Bloom:
- *Size.*—Large. Average size when fully expanded, 3½" to 4".
- *Borne.*—Singly, in flat clusters.
- *Stems.*—Short.
- *Form.*—When first open, flat. Permanence—retains its form to the end.
- *Petalage.*—Number of petals under normal conditions, 40–45.
- *Color.*—Center of flower: Upper side of petals—Begonia (619). Reverse side of petals—Porcelain Rose (620/1). Outer petals: Upper side of petals—same as center petals. Base of petals: Primrose Yellow (601/3) in area not definitely outlined but blended into major petal color. General tonality from a distance—Begonia (619).
- *Discoloration.*—General tonality at end of first day: Begonia (619). When petals fall: Upper side—Porcelain Rose (620/1). Lower side—Porcelain Rose (620/3).
- *Fragrance.*—Slight.

Petals:
- *Texture.*—Thick.
- *Surface.*—Satiny.
- *Shape.*—Deltoid with rounded outer edge.
- *Form.*—Tips slightly recurved.
- *Arrangement.*—Imbricated.
- *Petaloids in center.*—Few.
- *Persistence.*—Drop off cleanly.
- *Lastingness.*—On the plant—long. As cut flowers—fair.

Reproductive parts:
- *Stamens, anthers.*—Medium. Color—yellow. Arrangement—regular around styles.
- *Stamens, filaments (threads).*—Long and short. Color—yellow.
- *Pollen.*—Golden yellow.
- *Stigmas.*—Color—light yellow.
- *Ovaries.*—All enclosed in calyx.

Fruit: (Not observed).

PLANT

Form: Climber.

Growth: Very vigorous.

Foliage: Number of leaflets on normal mid-stem leaves, 5.
- *Size.*—Very large.
- *Quantity.*—Abundant.

*Color.*—New foliage: Much darker than Garnet Brown (00918). Old foliage: Parsley Green (00962/3).

Leaflets:

*Shape.*—Oval pointed.

*Texture.*—Upper side—leathery. Underside—smooth. Ribs and veins—ordinary.

*Edge.*—Serrated.

*Serration.*—Single.

*Petiole (rachis).*—Color—Garnet Brown (00918/3), upper edges; Green, lower edges. Underside—prickles.

*Stipules.*—Long, serrated.

*Disease resistance.*—Very resistant to mildew, rust and blackspot, under normal growing conditions at Irvine, Calif.

Wood:

*New wood.*—Color—light green, heavily covered with Garnet Brown (00918/3). Bark—smooth.

*Old wood.*—Color—green. Bark—smooth.

Thorns:

*Quantity.*—On main stalks from base—ordinary. On laterals from stalk—ordinary.

*Form.*—Broad base, hooked downwardly.

*Color.*—Red.

*Position.*—Irregular.

Prickles:

*Quantity.*—On main stalks—none. On laterals—none.

Short needles:

*Quantity.*—On main stalks—none. On laterals—none.

I claim:

1. A new and distinct cultivar of rose plant of the climber class, substantially as herein shown and described, characterized particularly as to novelty by the unique combination of its climbing habit of growth; abundant, large mildew resistant folliage, large quantities of blooms of Begonia (*Wilson's*) color which change to Porcelain Rose (*Wilson's*); and habit of blooming in large clusters on ends of main canes and on short stems from lateral growth.

No references cited.

ROBERT E. BAGWILL, Primary Examiner